US012303639B2

(12) United States Patent
Petit (10) Patent No.: US 12,303,639 B2
(45) Date of Patent: May 20, 2025

(54) DEVICE FOR INHALATION-SYNCHRONISED DISPENSING OF A FLUID PRODUCT (71) Applicant: APTAR FRANCE SAS, Le Neubourg (FR)

(72) Inventor: Ludovic Petit, Vitot (FR)

(73) Assignee: APTAR FRANCE SAS, Le Neubourg (FR)

(*) Notice: Subject to any disclaimer, the term of this patent is extended or adjusted under 35 U.S.C. 154(b) by 1231 days.

(21) Appl. No.: 16/086,103

(22) PCT Filed: Apr. 13, 2017

(86) PCT No.: PCT/FR2017/050891
§ 371 (c)(1),
(2) Date: Sep. 18, 2018

(87) PCT Pub. No.: WO2017/178765
PCT Pub. Date: Oct. 19, 2017

(65) Prior Publication Data
US 2020/0297947 A1 Sep. 24, 2020

(30) Foreign Application Priority Data
Apr. 15, 2016 (FR) ...................................... 1653367

(51) Int. Cl.
*A61M 15/00* (2006.01)
*A61M 16/00* (2006.01)

(52) U.S. Cl.
CPC .... *A61M 15/0095* (2014.02); *A61M 15/0021* (2014.02); *A61M 15/008* (2014.02);
(Continued)

(58) Field of Classification Search
CPC .......... A61M 15/0095; A61M 15/0021; A61M 15/008; A61M 15/009; A61M 15/0025;
(Continued)

(56) References Cited

U.S. PATENT DOCUMENTS 3,456,644 A * 7/1969 Thiel ................. A61M 15/0091
128/200.23
4,819,834 A * 4/1989 Thiel ..................... G01F 11/021
222/402.2
(Continued)

FOREIGN PATENT DOCUMENTS

DE 30 40 641 A1 5/1982
EP 0 441 643 A1 8/1991
(Continued)

OTHER PUBLICATIONS

Merriam Webster, "Tab Definition," 2015. (Year: 2015).*
(Continued)

*Primary Examiner* — Timothy A Stanis
(74) *Attorney, Agent, or Firm* — Sughrue Mion, PLLC (57) ABSTRACT

An inhalation-synchronized fluid dispenser device having a body with a mouthpiece, a fluid reservoir containing a fluid and a propellant gas mounted to slide axially in the body, a metering valve including a valve member assembled on the reservoir, an actuator element movable and/or deformable between a non-actuation position in which the metering valve cannot be actuated, and an actuation position in which the metering valve can be actuated; and an inhalation-controlled trigger system including an inhalation-sensitive member deformable and/or movable under the effect of inhaling. The inhalation-sensitive member moves and/or deforms the actuator element from its non-actuation position towards its actuation position. The actuator element is a blocking element that, in the non-actuation position, co-operates firstly with the body and secondly with the reser- (Continued)

voir to prevent the reservoir from moving axially in the body.

7 Claims, 7 Drawing Sheets

(52) U.S. Cl.
CPC ....... *A61M 15/009* (2013.01); *A61M 15/0025* (2014.02); *A61M 2016/0021* (2013.01); *A61M 2205/276* (2013.01); *A61M 2205/3331* (2013.01); *A61M 2205/3553* (2013.01); *A61M 2205/3561* (2013.01); *A61M 2205/3584* (2013.01); *A61M 2205/3592* (2013.01); *A61M 2205/502* (2013.01); *A61M 2205/52* (2013.01)

(58) Field of Classification Search
CPC .... A61M 2016/0021; A61M 2205/276; A61M 2205/3331; A61M 2205/3553; A61M 2205/3561; A61M 2205/3584; A61M 2205/3592; A61M 2205/502; A61M 2205/52; A61M 15/00; A61M 15/0013; A61M 15/002; A61M 15/0065; A61M 15/0068; A61M 15/0091; A61M 15/0093; A61M 16/208; A61M 2202/0007; A61M 2210/0625; A61M 2205/3546; A61M 2205/82; A61M 2205/27
USPC .................................................... 128/204.26
See application file for complete search history.

(56) References Cited

U.S. PATENT DOCUMENTS

| | | | | |
|---|---|---|---|---|
| 5,027,808 A * | 7/1991 | Rich | ................ | A61M 15/0091 128/200.23 |
| 5,060,643 A * | 10/1991 | Rich | ................ | A61M 15/0091 128/200.14 |
| 5,119,806 A * | 6/1992 | Palson | .............. | A61M 15/0096 128/200.14 |
| 5,507,281 A * | 4/1996 | Kuhnel | ............ | A61M 15/0091 128/203.23 |
| 6,397,839 B1 * | 6/2002 | Stradella | ........... | A61M 15/0081 128/200.14 |
| 7,302,948 B2 * | 12/2007 | Anderson | ........... | B05B 11/3091 128/200.22 |
| 7,543,582 B2 * | 6/2009 | Lu | ....................... | A61M 15/008 128/200.23 |
| 8,578,932 B2 * | 11/2013 | Andersen | .......... | A61M 15/0091 128/200.14 |
| 10,029,845 B2 * | 7/2018 | Jinks | ................. | B65D 83/546 |
| 10,335,562 B2 * | 7/2019 | Jinks | ................. | A61M 15/009 |
| 10,751,154 B2 * | 8/2020 | Rahmel | .................. | B65D 83/22 |
| 2004/0231667 A1 * | 11/2004 | Horton | ................ | A61M 15/008 128/202.13 |
| 2005/0109336 A1 * | 5/2005 | Stradella | ........... | A61M 15/0091 128/200.23 |
| 2008/0210231 A1 * | 9/2008 | Kakade | ............... | A61M 15/009 128/200.23 |
| 2015/0297843 A1 * | 10/2015 | Lu | ..................... | A61M 15/0076 128/200.23 |
| 2015/0306321 A1 * | 10/2015 | Stuart | .................... | B65D 83/54 222/402.1 |
| 2019/0130790 A1 * | 5/2019 | Baker | ................. | A61M 15/009 |

FOREIGN PATENT DOCUMENTS

| | | | |
|---|---|---|---|
| EP | 3578218 A1 * | 12/2019 | .......... A61M 15/009 |
| FR | 2 775 668 A1 | 9/1999 | |
| WO | 85/01880 A1 | 5/1985 | |

OTHER PUBLICATIONS

International Search Report for PCT/FR2017/050891 dated Jun. 27, 2017 [PCT/ISA/210].
International Preliminary Report on Patentability dated Oct. 18, 2018 issued by the International Bureau in PCT/FR2017/050891.

* cited by examiner

DEVICE FOR INHALATION-SYNCHRONISED DISPENSING OF A FLUID PRODUCT

CROSS REFERENCE TO RELATED APPLICATIONS

This application is a National Stage of International Application No. PCT/FR2017/050891, filed on Apr. 13, 2017, which claims priority from French Patent Application No. 1653367, filed on Apr. 15, 2016.

The present invention relates to a fluid dispenser device in which dispensing is synchronized with inhaling, and more particularly it relates to an inhaler device of the aerosol type synchronized with inhaling.

Breath actuated inhaler (BAI) devices are well known in the state of the art. The main advantage of this type of device is that the dispensing of fluid is synchronized with the patient inhaling, so as to guarantee that the fluid is properly dispensed into the airways. Thus, in the field of aerosol devices, i.e. devices in which the fluid is dispensed by means of a propellant gas, numerous types of breath actuated inhaler device have been proposed. However, those devices present the drawback of including a large number of parts, i.e. they are complicated and costly to manufacture and to assemble, which is obviously disadvantageous. It is also difficult to find the right balance between reliable triggering on each inhalation, without the actuation threshold being too high, and a latch that is robust enough to prevent accidental of unwanted actuation. Unfortunately, when the latch releases accidentally, the device is actuated automatically and the dose is dispensed, even when the user does not want it.

Thus, in order to dispense the dose properly, what is more important than actuating the device automatically, is for dispensing to be synchronized with the user inhaling, even if actuation or triggering remains manual.

Document FR 2 775 668 describes a prior-art device.

An object of the present invention is to provide an inhalation-synchronized fluid dispenser device that does not have the above-mentioned drawbacks.

Another object of the present invention is to provide an inhalation-synchronized fluid dispenser device that improves operational reliability by guaranteeing effective actuation on each inhalation.

Another object of the present invention is to provide an inhalation-synchronized fluid dispenser device that minimizes the risks of accidental or unwanted actuation.

Another object of the present invention is to provide an inhalation-synchronized fluid dispenser device that does not present an actuation threshold that is too high, thereby making it possible for people who are relatively weak, such as the sick or the elderly, to use the device in safe and reliable manner.

Another object of the present invention is to provide an inhalation-synchronized fluid dispenser device that is simple and inexpensive to manufacture and to assemble.

The present thus provides an inhalation-synchronized fluid dispenser device comprising a body provided with a mouthpiece, a fluid reservoir containing a fluid and a propellant gas being mounted to slide axially in said body, a metering valve including a valve member being assembled on said reservoir for selectively dispensing the fluid, said device further comprising:

an actuator element that is movable and/or deformable between a non-actuation position in which said metering valve cannot be actuated, and an actuation position in which said metering valve can be actuated; and an inhalation-controlled trigger system including an inhalation-sensitive member that is deformable and/or movable under the effect of inhaling, said inhalation-sensitive member, when it is deformed and/or moved, moving and/or deforming said actuator element from its non-actuation position towards its actuation position, said actuator element being a blocking element that, in the non-actuation position, co-operates firstly with the body and secondly with the reservoir so as to prevent said reservoir from moving axially in the body.

Advantageously, said actuator element is a blocking ring that is fastened, in particular snap-fastened, on said reservoir, and that includes at least one axial tab, in particular three axial tabs, that co-operate with a shoulder that is secured to said body so as to prevent said reservoir from moving axially in said body.

Advantageously, said at least one axial tab is deformable radially outwards so as to pass from the non-actuation position towards the actuation position, a trigger element being provided so as to hold said at least one axial tab in the non-actuation position.

Advantageously, said trigger element is mounted to move between a blocking position in which it blocks said blocking ring in its non-actuation position, and a release position in which it does not block said blocking ring.

Advantageously, said inhalation-controlled trigger system includes a deformable membrane that defines a deformable air chamber, said deformable membrane being fastened to said trigger element, said deformable membrane being deformed during inhaling, so that it moves said trigger element from its blocking position towards its release position.

Advantageously, said trigger element is accessible to the user through at least one opening in the body, so that it can be moved manually towards its release position even in the absence of inhaling.

Advantageously, said blocking element comprises an axial extension having a bottom end that is fastened radially and axially relative to said body, and a top end that co-operates with said reservoir in the non-actuation position.

Advantageously, said inhalation-controlled trigger system includes a piston that slides in a chamber between a rest position and an inhaling position.

Advantageously, said blocking element is assembled on a rod that is secured to the piston, so that during inhaling, said rod moves radially, deforming and/or moving said axial extension towards its actuation position.

Advantageously, said device includes an electronic dose counter.

Advantageously, said device includes signal-transmitter means for communicating, in particular communicating remotely, information relating to the actuations of the device.

These characteristics and advantages and others appear more clearly from the following detailed description, given by way of non-limiting example, and with reference to the accompanying drawing, in which.

Figure 1:
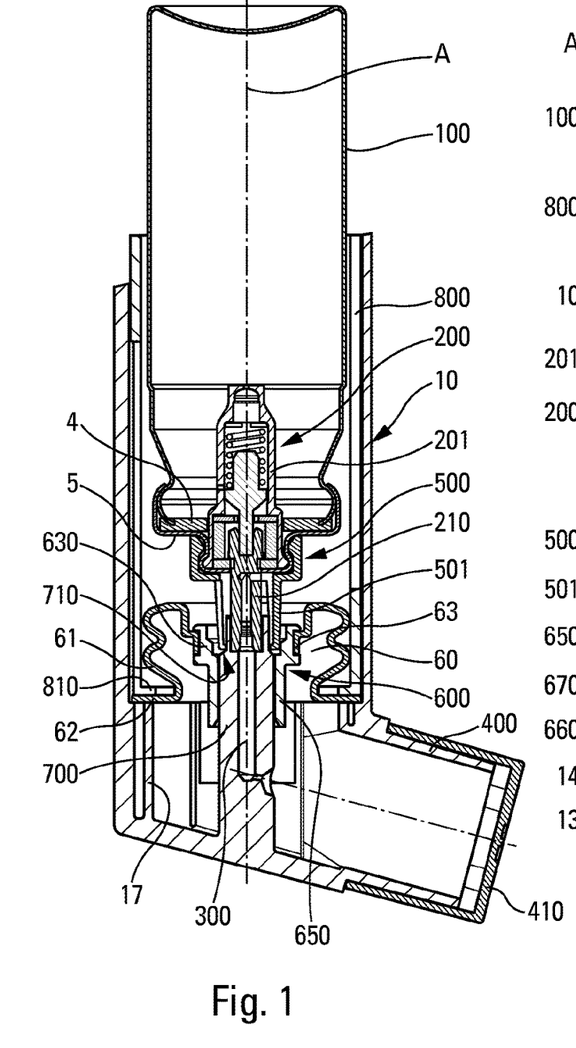
FIG. 1 is a diagrammatic section view of a fluid dispenser device, in a first advantageous embodiment, in the rest position.

In the description, the terms "top", "bottom", "upwards", and "downwards" refer to the upright position of the device shown in particular in FIG. 1. The terms "axial" and "radial" are relative to the vertical central axis A shown in particular in FIG. 1. The terms "proximal" and "distal" are relative to the mouthpiece.

The invention applies more particularly to inhaler devices of the aerosol-valve type for oral dispensing, as described in greater detail below, but it could also apply to other types of inhaler device, e.g. of the nasal type.

The figures show several advantageous embodiments of the invention, but naturally one or more of the component parts described below could be made in some other way, while providing functions that are similar or identical.

Figure 8:
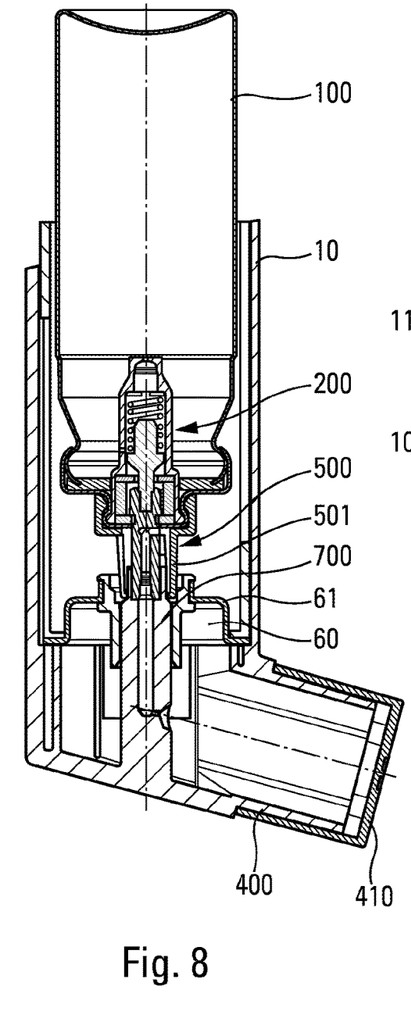
FIG. 8 is a diagrammatic section view of a variant embodiment of the air chamber, in the rest position.
Figure 9:
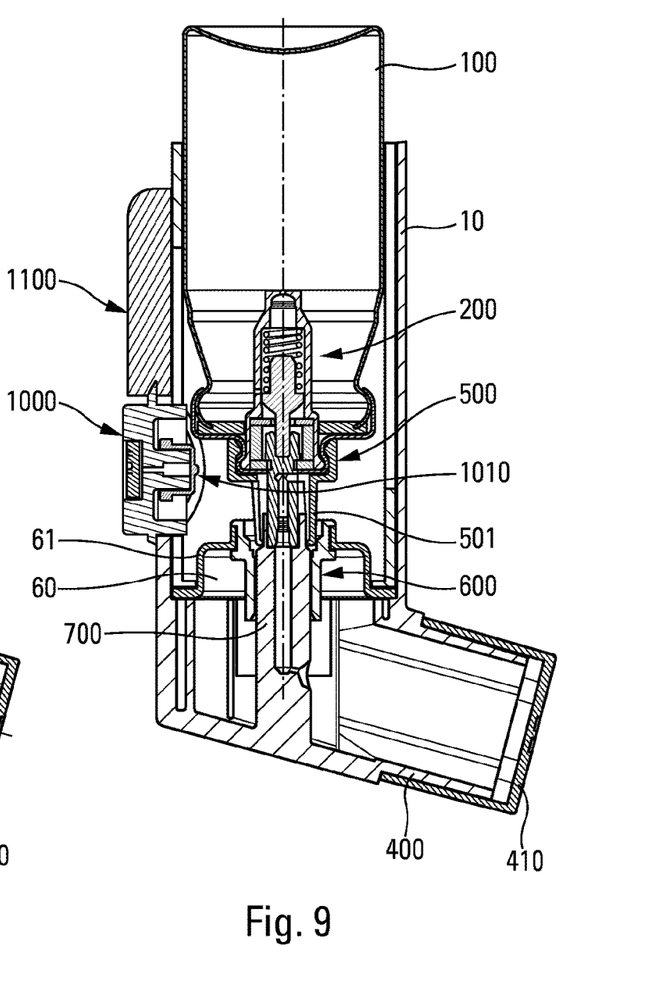
FIG. 9 is a view similar to the view in FIG. 8, showing another variant embodiment incorporating electronics, in the rest position.

With reference to the drawings, the device includes a main body 10 provided with a mouthpiece 400. The mouthpiece 400 defines a dispenser orifice through which the user inhales while the device is being used. A removable protective cap 410 may be provided on said mouthpiece 400, in particular while it is being stored, that the user removes before use. FIGS. 1, 8, and 9 show such a protective cap that could be of any shape.

The body 10 contains a reservoir 100 that contains the fluid to be dispensed and a propellant gas, such as a gas of the hydrofluoroalkane (HFA) type, a metering valve 200 being mounted on said reservoir 100 for selectively dispensing the fluid. The metering valve 200 comprises a valve body 201, and a valve member 210 that, during actuation, is axially movable relative to said valve body 201, and thus relative to said reservoir 100. The metering valve 200 can be of any appropriate type. It may be fastened to the reservoir 100 via a fastener element, preferably a crimped cap 5, preferably with a neck gasket 4 interposed therebetween.

Advantageously, during actuation, the valve member 210 is stationary relative to the body 10, and it is the reservoir 100 that is moved axially relative to the body between a distal position, that is the rest position, and a proximal position.

The outlet orifice of the valve member 210 of said metering valve 200 is connected via a channel 300 to said mouthpiece 400 through which the user inhales the fluid to be dispensed. In known manner, said valve member 210 is received in a valve well 700 that defines said channel 300, at least in part. In the embodiments in FIGS. 1 to 9, the valve well is formed integrally with the body 10, while in the embodiments in FIGS. 14 to 19, said valve well is axially movable relative to said body 10.

In the invention, the device includes an actuator element 500, 500' that is movable and/or deformable between a non-actuation position in which said metering valve 200 cannot be actuated, and an actuation position in which said metering valve 200 can be actuated. In the rest position, said actuator element 500, 500' is in the non-actuation position, and it is the user inhaling through the mouthpiece 400 that moves and/or deforms said actuator element 500, 500' towards its actuation position. In other words, so long as the user does not inhale, it is impossible to actuate the metering valve 200, and it is only when the user inhales that the metering valve 200 can be actuated, advantageously by pressing manually on the bottom of the reservoir 100.

As described in greater detail below, the actuator element is a blocking element 500, 500' that, in the non-actuation position, prevents the reservoir 100 from moving axially in the body 10. During inhaling, the blocking element 500, 500' is moved and/or deformed so that it no longer prevents the reservoir 100 from moving axially in the body 10. Thus, after inhalation, such an axial movement of the reservoir 100 causes the metering valve 200 to be actuated and a dose of fluid to be dispensed, synchronously with the inhaling.

Thus, in the absence of inhaling, there is no risk of an active dose of fluid being lost by accidental or incomplete actuation during which the user does not inhale. Actuating the valve 200 and expelling a dose of fluid are thus possible only when the user inhales and simultaneously presses on the reservoir 100 so as to actuate the valve 200.

The device includes a trigger system that is controlled by the user inhaling, and that is for moving and/or deforming said actuator element 500, 500' from its non-actuation position towards its actuation position, when the user inhales through the mouthpiece 400.

The trigger system includes an inhalation-sensitive member 60, 65 that is deformable and/or movable under the effect of inhaling, the inhalation-sensitive member 60, 65 being adapted, when it is deformed and/or moved, to move and/or deform said actuator element 500, 500' from its non-actuation position towards its actuation position.

As described in greater detail below, the inhalation-sensitive member may be made in the form of a deformable air chamber 60, e.g. a bellows or a deformable pouch.

In a variant, as described with reference to FIGS. 14 to 16, the inhalation-sensitive member may be made in the form of a piston 65 that is preferably cylindrical, and that slides in a chamber 66 that is preferably cylindrical and non-deformable.

In a first embodiment shown in FIGS. 1 to 13, the non-actuation position corresponds to a position in which the reservoir 100 is blocked in the body 10. In this blocked position, the reservoir 100 is prevented from moving by said actuator element that is released only at the moment of inhaling.

Figure 10:
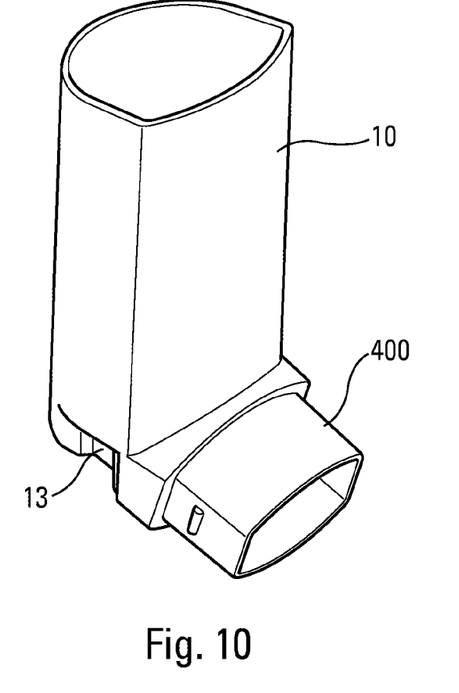
FIG. 10 is a diagrammatic detail view in perspective of the FIG. 1 body.

The body 10 is shown in particular in FIG. 10. Naturally, this shape shown is not limiting.

Figure 11:
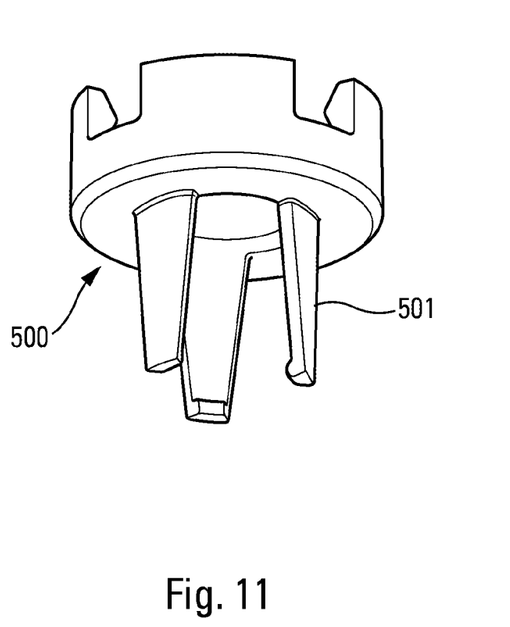
FIG. 11 is a diagrammatic detail view in perspective of the FIG. 1 blocking ring.

In this embodiment, the actuator element, forming the blocking element, is advantageously formed by a blocking ring 500 that includes at least one, and preferably three, axial blocking tabs 501 that are elastically deformable radially outwards. FIG. 11 is a perspective view of the blocking ring 500. The blocking ring 500 is fastened, in particular snap-fastened, on the reservoir 100, in particular on the cap 5 that fastens the metering valve 200 on the reservoir 100. In the rest position, said blocking tabs 501 bear against a radial shoulder 710 of said valve well 700. The shoulder preferably slopes downwards and radially outwards, such that when the reservoir 100 slides axially in the body 10 during actuation, said axial blocking tabs 501 slide over said sloping shoulder 710, thereby deforming them radially outwards.

A trigger element 600 is mounted around said valve well 700 to slide axially between a blocking position in which it blocks said blocking ring 500 in its non-actuation position, and a release position in which it no longer blocks said blocking ring 500. In particular, in the embodiment in FIGS. 1 to 13, said trigger element 600, in the blocking position, co-operates with said blocking tabs 501, preventing any deformation radially outwards of said blocking tabs 501. Thus, when said trigger element 600 is in the blocking position, it prevents said blocking tabs 501 from deforming radially outwards, which blocking tabs consequently remain blocked axially by said shoulder 710 of the valve well 700, thereby preventing the reservoir 100 from moving axially and the metering valve 200 from being actuated. Optionally, slide means, such as balls, could be interposed between the valve well 700 and the trigger element 600, so as to make it easier for said trigger element to slide during inhaling.

Figure 12:
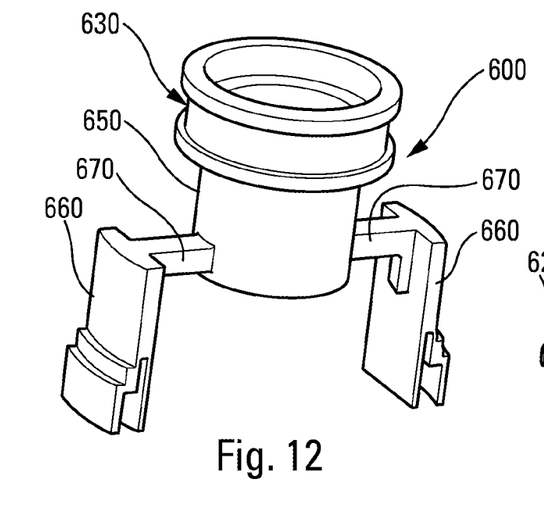
FIG. 12 is a diagrammatic detail view in perspective of the FIG. 1 trigger element.

As can be seen more particularly in FIG. 12, the trigger element 600 advantageously comprises an axially slidable hollow central sleeve 650 around the valve well 700, and two axial tabs 660 that are diametrically-opposite and each of which is connected to said central sleeve 650 via a respective radial spacer 670. Each of the axial tabs 660 co-operates with a respective opening 13 of the body 10, for substantially closing the openings 13 in the blocking position, and for substantially opening the openings 13 in the release position. Since the openings 13 are closed at the start of inhaling, the inhalation flow due to inhaling initially passes mainly to the trigger system, in this embodiment the deformable air chamber 60. This makes it possible to optimize such triggering by inhaling. When the trigger element 600 is moved axially towards its release position under the effect of inhaling, and thus when the user can actuate the metering valve 200 so as to dispense a dose of fluid, the axial tabs 660 open said openings 13 of the body 10, and this draws in air and thus increases the inhalation flow. This optimizes synchronization between the user inhaling and dispensing the dose, and also promotes good dispensing of the dose into the user's lungs.

Advantageously, said axial tabs 660 are accessible from the outside through said openings 13. This makes it possible, if necessary, to move the trigger element 600 manually, so as to be able to actuate the metering valve 200 even without inhaling, e.g. when the person that needs to receive the dose of fluid is incapable of inhaling sufficiently. This is thus a safety measure. In a variant to this safety measure, an axial extension (not shown) could be provided that is secured to the trigger element 600, e.g. extending sideways from the reservoir 100, and accessible to the user from the outside of the body 10.

Figure 2:
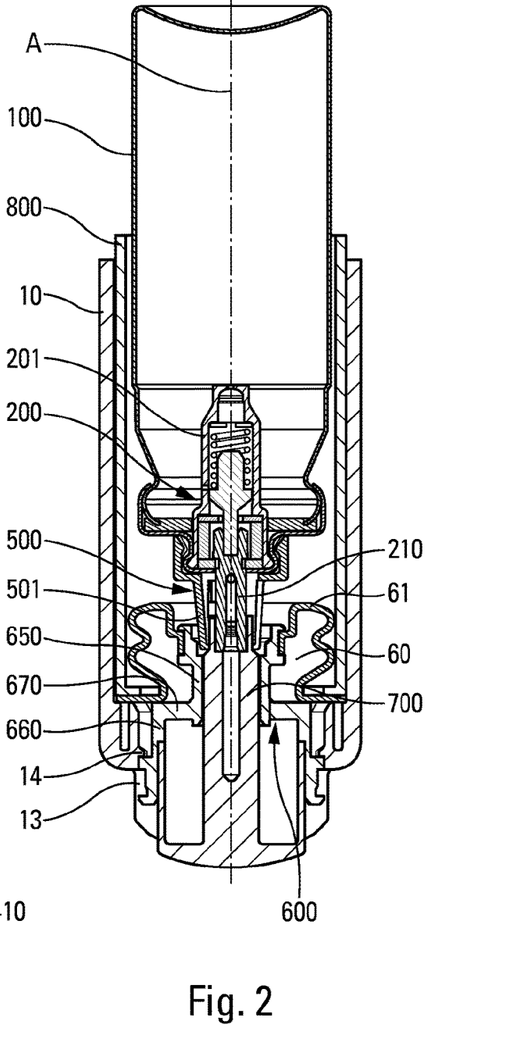
FIG. 2 is a view similar to the view in FIG. 1, in another vertical section plane.
Figure 5:
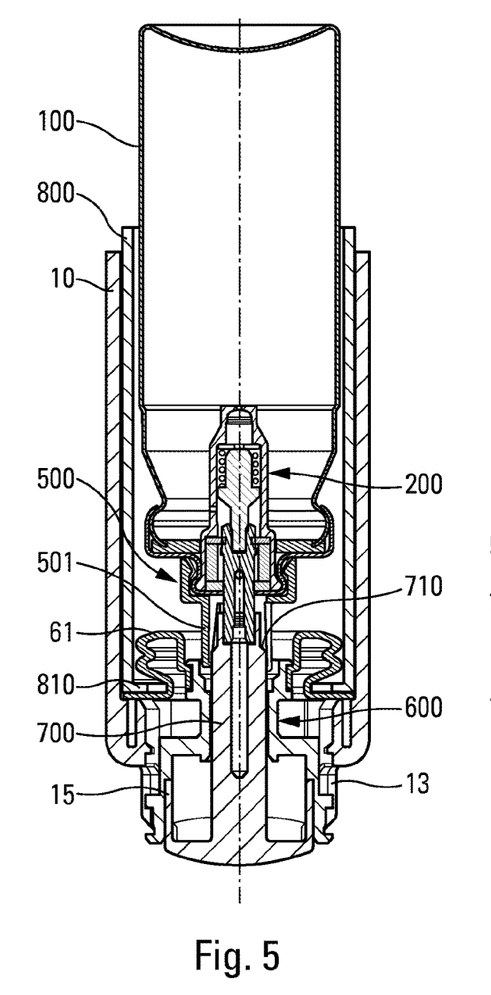
FIG. 5 is a view similar to the view in FIG. 2, in the position for dispensing a dose of fluid.

Advantageously, and as can be seen in FIG. 2, said axial tabs 660 co-operate with a first shoulder 14 of the body 10 so as to define the blocking position of the trigger element 600, by forming an axial abutment that prevents said trigger element 600 from rising upwards beyond the blocking position. Likewise, and as can be seen in FIG. 5, said axial tabs 660 co-operate with a second shoulder 15 of the body 10 so as to define the release position of the trigger element 600, by forming an axial abutment that prevents said trigger element 600 from moving downwards beyond the release position.

In a variant (not shown), the trigger element 600 need not include axial tabs 660, and the body would thus not include the openings 13. In this configuration, the inhalation flow could flow axially in the body, around the valve well, which could be encouraged by a central sleeve 650 provided with axial cutouts for passing the flow of air.

Figure 13:
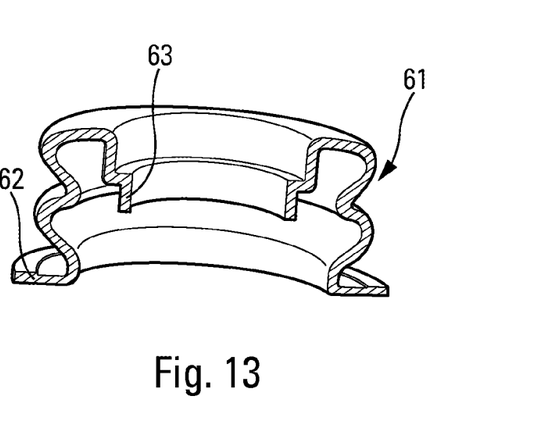
FIG. 13 is a diagrammatic detail view in section and in perspective of the FIG. 1 deformable membrane.

In the embodiment in FIGS. 1 to 13, the inhalation-sensitive member 60 is made in the form of a deformable air chamber. Advantageously, the air chamber comprises a deformable membrane 61 that is connected firstly to the body 10 and secondly to said trigger element 600. Advantageously, as can be seen in FIGS. 1 to 9, a membrane-carrier sleeve 800 is arranged in stationary manner in the body 10, with a bottom shoulder 810 that jams a first edge 62 of the membrane 61 against a portion 17 of the body 10. The second edge 63 of the membrane 61 may be fastened in a channel 630 of the trigger element 600, advantageously formed in the hollow central sleeve 650 of said trigger element. FIG. 13 is a section view of a membrane in the form of bellows, but other forms are possible, in particular a mere pouch or diaphragm, as can be seen in FIG. 8.

During inhaling, the deformable membrane 61 deforms and/or contracts under the effect of the suction generated by inhaling, causing the trigger element 600 to move from its blocking position towards its release position. This then enables said blocking tabs 501 to deform, and thus enables said blocking ring 500 that forms the actuator element to move from its non-actuation position towards its actuation position. FIGS. 1 to 7 show a deformable membrane 61 made in the form of a bellows, and FIG. 8 shows a variant in which the deformable membrane is made in the form of a pouch or a diaphragm. Naturally, other forms can also be envisaged.

The valve 200 is thus actuated only at the moment of inhaling, such that the dose of fluid is expelled out of the dispenser orifice simultaneously with inhaling.

Figure 3:
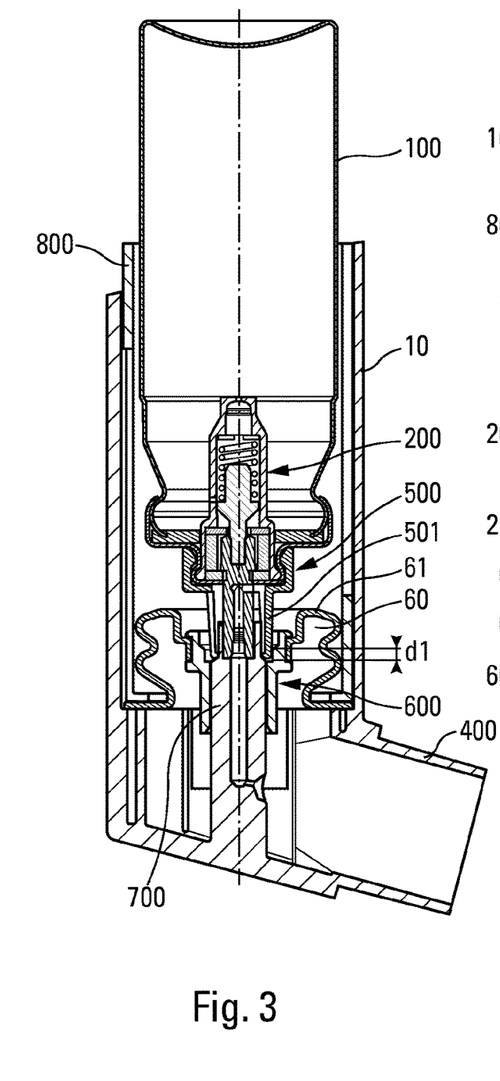
FIG. 3 is a view similar to the view in FIG. 1, in the non-dispensing position before suction.

When the user wishes to use the device, the user places the mouthpiece 400 in the mouth, and presses manually on the bottom of the reservoir 100, i.e. the top surface of said reservoir 100 in the position in the figures. The reservoir 100 is then blocked and prevented from sliding in the body 10 by the blocking tabs 501 of the blocking ring 500, which blocking tabs bear against the shoulder 710 of the valve well 700. Optionally, the reservoir 100 may perform a short stroke d1 before becoming blocked, this initial small stroke d1 however being insufficient to actuate the metering valve 200. FIG. 1 shows the device at rest, and FIG. 3 shows the device in the position with the reservoir 100 blocked, after said reservoir has made the initial small stroke d1.

Figure 4:
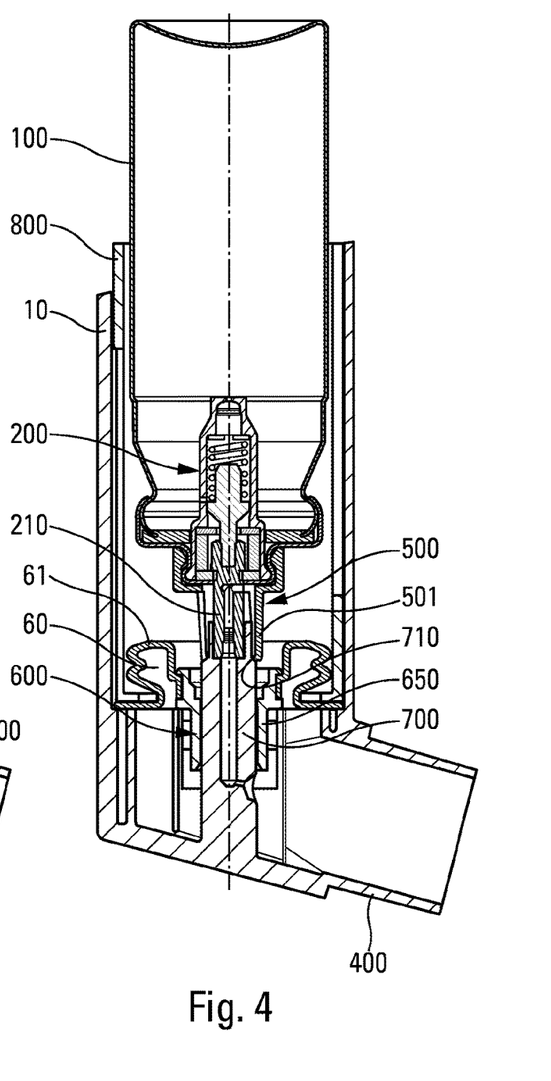
FIG. 4 is a view similar to the view in FIG. 3, in the position after suction.
Figure 6:
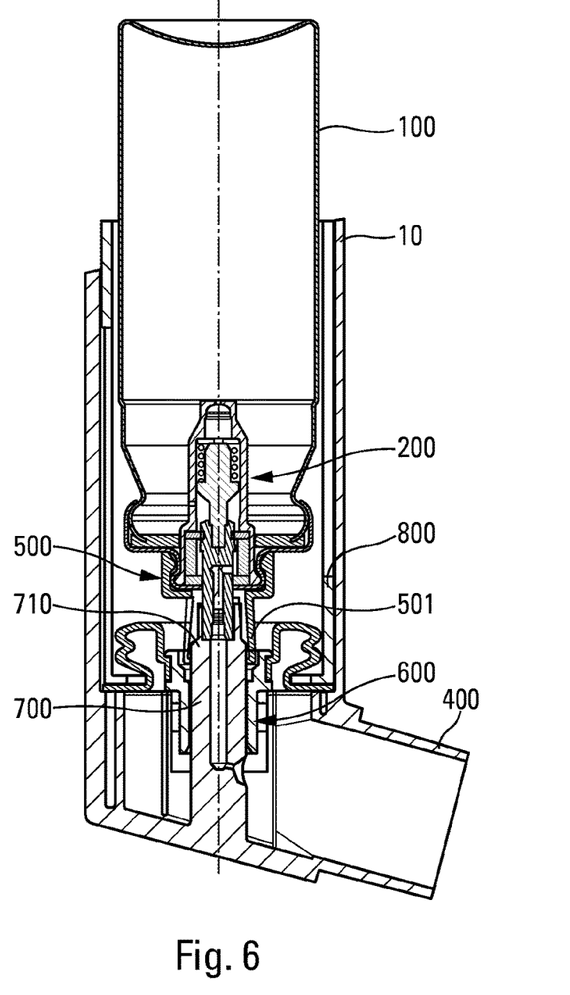
FIG. 6 is a view similar to the view in FIG. 5, in another vertical section plane.

When the user inhales through the mouthpiece 400, the deformable membrane 61 deforms, and this causes the trigger element 600 that is fastened to said deformable membrane 61 to slide, as can be seen in FIG. 4. The movement of the trigger element 600 over the valve well 700 releases the tabs 501 of the blocking ring 500 radially. Under the effect of the axial force transmitted by the reservoir 100, generated by the user who is pressing on the bottom of said reservoir 100, the axial tabs 501 are able to deform radially outwards, and thus pass over said shoulder 710, so as to enable the reservoir 100 to slide towards its dispensing position, and the valve 200 thus to be actuated. This dispensing position is shown in FIGS. 5 and 6.

Figure 7:
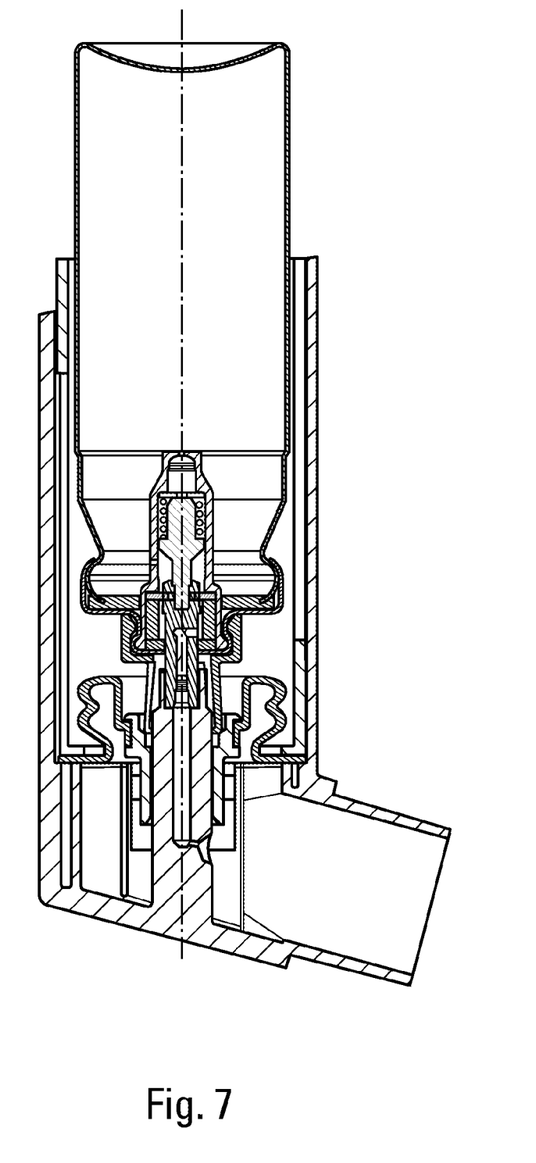
FIG. 7 is a view similar to the view in FIG. 6, in the position after dispensing a dose of fluid.

At the end of inhaling, the trigger element 600 is returned upwards by the springiness of the membrane 61. FIG. 7 shows the position in which the trigger element 600 has been returned by said membrane 61, but before the user releases the pressure on the reservoir 100.

When the user releases the pressure on the bottom of the reservoir 100, said reservoir returns towards the rest position under the effect of the return spring of the valve 200, and the valve member 210 of the metering valve simultaneously returns to the rest position, once again filling the valve chamber with a new dose of fluid. The device is thus ready for another utilization.

FIG. 9 shows a variant embodiment of the FIG. 8 embodiment, carrying electronic modules.

In particular, an electronic dose counter 1000 is provided, advantageously assembled on the body 10. In particular, the counter 1000 can detect the movements of the reservoir 100, e.g. by means of a contact sensor 1010. In a variant, the counter 1000 could be connected to a sensor, in particular a membrane sensor, that detects the dose of fluid being dispensed, e.g. in the valve well 700. The electronic counter 1000 may be actuated in other ways, e.g. by detecting the movement of the valve member 210 of the metering valve relative to the valve body 201.

Preferably, the device also includes signal-transmitter means 1100 for communicating, in particular communicating remotely, information relating to the actuations of the device. In particular, the body 10 may include a signal-transmitter module, for communicating remotely with any base. Appropriate power supply means are advantageously provided.

In particular, the electronic module may advantageously comprise a card that includes an electrical switch that sends a pulse. The module may also comprise a display and/or use a Bluetooth or Wifi connection for sending information to an accompanying peripheral. Appropriate sensors, such as flowrate and/or pressure sensors, may be provided for detecting various parameters of the inhalation flow.

Associated with a dose counter 1000 that counts each dose that is actually dispensed, and with the inhalation-synchronized device of the invention, the signal-transmitter means 1100 make it possible for each dose that has been dispensed to be transmitted in completely reliable manner, e.g. to a doctor or to any other person wishing to monitor the use of the inhaler device by the user. The inhalation-synchronized device guarantees that the user inhales each time the user actuates the device, and the counter records each dose that is dispensed, together with various associated parameters, such as a timestamp for each dispensing. In this way, the doctor can know very accurately the conditions of use of the device by the user.

Figure 14:
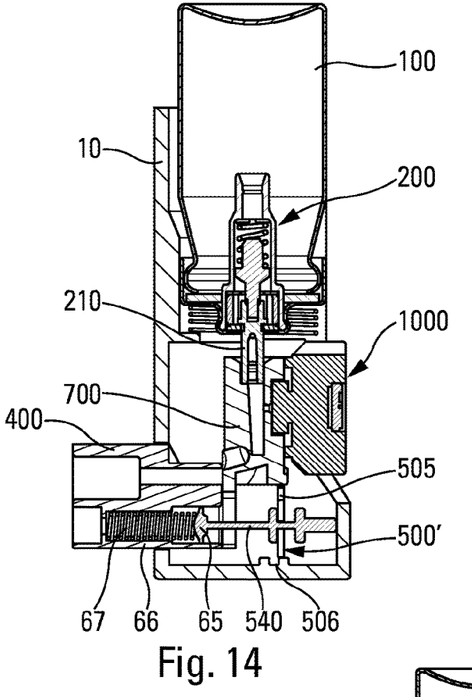
FIG. 14 is a diagrammatic section view of a fluid dispenser device, in still another advantageous embodiment, in the rest position.
Figure 15:
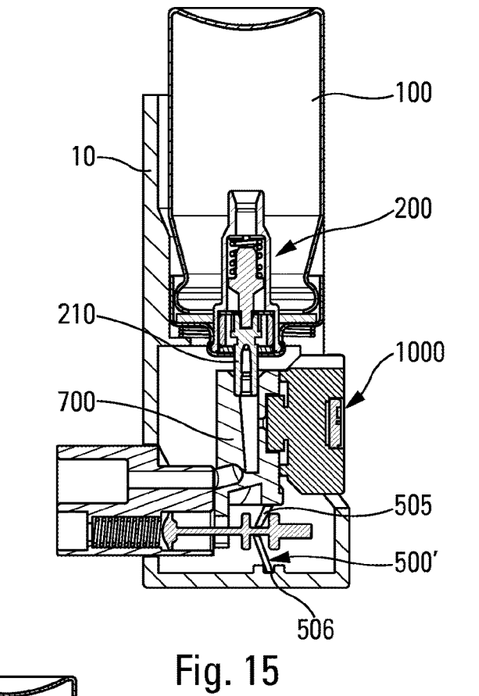
FIG. 15 is a view similar to the view in FIG. 14, in the dispensing position.
Figure 16:
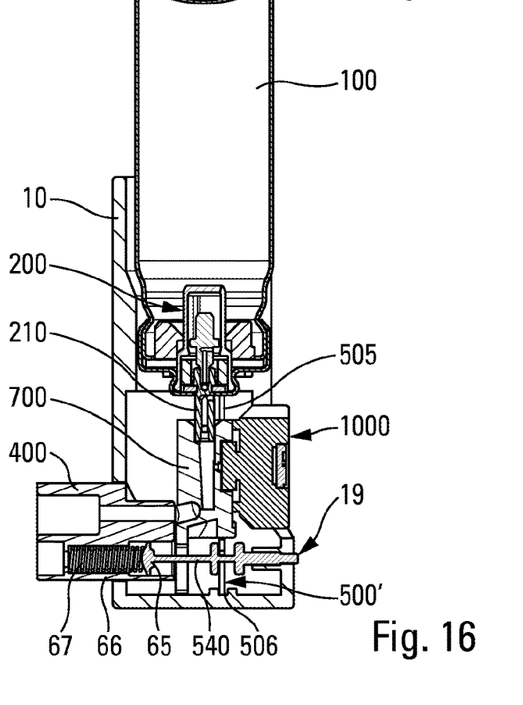
FIG. 16 is a view similar to the view in FIG. 14, showing a variant embodiment.

FIGS. 14 to 16 show another embodiment in which the actuator element is made in the form of a blocking element 500' that, in the non-actuation position, prevents the reservoir 100 from moving axially in the body 10. During inhaling, the blocking element 500' is moved and/or deformed so that it no longer prevents the reservoir 100 from moving axially in the body 10. Thus, after inhaling, such axial movement of the reservoir 100 causes the metering valve 200 to be actuated and a dose of fluid to be dispensed, synchronously with the inhaling.

In this embodiment, the inhalation-sensitive member is made in the form of a piston 65 that slides in a chamber 66 between a rest position and an inhaling position. The chamber 66 is advantageously formed in the mouthpiece 400. A rod 540 is connected to said piston 65. A spring 67, advantageously arranged in the chamber 66, is adapted to return said piston 65 towards its rest position when there is no longer any inhaling through the mouthpiece 400.

When the user inhales through the mouthpiece 400, the piston 65 moves radially (relative to the movement axis of the reservoir 100 in the body 10) in the chamber 66 under the effect of the suction created by inhaling.

In particular, the blocking element 500' may be assembled on said rod 540 that is secured to the piston 65, and may include an axial extension 505 that, in the non-actuation position, extends axially in the body so as to co-operate with said reservoir 100 and block it axially. When the user inhales, the rod 540 moves radially towards the left (in the orientation in the figures), and this causes said axial extension 505 to deform, and thus to release the reservoir 100 to move axially. In the embodiment shown, the valve well 700 is mounted to move in the body 10, but it could also be stationary.

Advantageously, the bottom end 506 of said axial extension 505 is fastened radially and axially relative to the body 10. Thus, when the rod 540 moves radially, it pulls radially on said axial extension which deforms, e.g. bends or pivots, such that the top end is disengaged from the reservoir 100 and releases said reservoir so as to enable it to move axially. Naturally, the blocking element 500' could be of any other appropriate form. In particular, it is possible to envisage using a hinged toggle.

FIG. 16 shows a variant embodiment in which the rod 540 is accessible from the outside of the body 10 through an opening 19 of said body 10. This makes it possible, where necessary, to move the blocking element 500' manually, so as to be able to actuate the metering valve 200 even without inhaling, e.g. when the person that needs to receive the dose of fluid is incapable of inhaling sufficiently. This is thus a safety measure.

The device shown in FIGS. 14 to 16 may also include electronic means, such as the electronic means described above in relation to FIG. 9. They are thus not described again.

The present invention applies, in particular, to treating asthma attacks or chronic obstructive pulmonary disease (COPD), by using formulations of the following types: salbutamol, aclidinium, formoterol, tiotropium, budesonide, fluticasone, indacaterol, glycopyrronium, salmeterol, umeclidinium bromide, vilanterol, olodaterol, or striverdi, or any combination of these formulations.

The present invention is described above with reference to various advantageous embodiments and variants, but naturally any useful modification could be applied thereto by the person skilled in the art, without going beyond the ambit of the present invention, as defined by the accompanying claims.

The invention claimed is:

1. An inhalation-synchronized fluid dispenser device comprising:
   a body provided with a mouthpiece, a reservoir containing a fluid and a propellant gas, the reservoir configured to be axially slidable in said body during actuation, a metering valve including a valve member being assembled on said reservoir for selectively dispensing the fluid;
   an actuator element that is movable and/or deformable between a non-actuation position wherein the reservoir is axially blocked to preclude said metering valve from being actuated, and an actuation position wherein the reservoir is configured to axially slide in the body to permit said metering valve to be actuated; and an inhalation-controlled trigger system including an inhalation-sensitive member that is deformable and/or movable under the effect of inhaling, said inhalation-sensitive member, when deformed and/or moved, moving and/or deforming said actuator element from its non-actuation position towards its actuation position;

said actuator element being a blocking element that, in the non-actuation position, co-operates with the body and with the reservoir so as to prevent said reservoir from moving axially in the body, wherein said actuator element is a blocking ring that is fastened on said reservoir and includes at least one axial tab that co-operates with a shoulder that is secured to said body so as to prevent said reservoir from moving axially in said body;

wherein said at least one axial tab is deformable radially outwards so as to pass from the non-actuation position towards the actuation position, a trigger element being provided so as to hold said at least one axial tab in the non-actuation position;

wherein said trigger element is mounted to move between a blocking position that blocks said blocking ring in the non-actuation position, and a release position that does not block said blocking ring; and wherein said inhalation-controlled trigger system includes a deformable membrane that defines a deformable air chamber, said deformable membrane being fastened to said trigger element, said deformable membrane being deformed during inhaling to move said trigger element from the blocking position towards the release position.

2. The device according to claim 1, wherein said trigger element is accessible to the user through at least one opening in the body, so that said trigger element is movable manually towards the release position even in the absence of inhaling.

3. The device according to claim 1, further comprising an electronic dose counter.

4. The device according to claim 1, further comprising a signal-transmitter that communicates remotely information relating to actuations of the device.

5. The device according to claim 1, wherein the blocking ring is snap-fastened on said reservoir.

6. An inhalation-synchronized fluid dispenser device comprising:

a body provided with a mouthpiece, a reservoir containing a fluid and a propellant gas, the reservoir configured to be axially slidable in said body during actuation, a metering valve including a valve member being assembled on said reservoir for selectively dispensing the fluid;

an actuator element that is movable and/or deformable between a non-actuation position wherein the reservoir is axially blocked to preclude said metering valve from being actuated, and an actuation position wherein the reservoir is configured to axially slide in the body to permit said metering valve to be actuated; and an inhalation-controlled trigger system including an inhalation-sensitive member that is deformable and/or movable under the effect of inhaling, said inhalation-sensitive member, when deformed and/or moved, moving and/or deforming said actuator element from its non-actuation position towards its actuation position;

said actuator element being a blocking element that, in the non-actuation position, co-operates with the body and with the reservoir so as to prevent said reservoir from moving axially in the body, wherein said actuator element is a blocking ring that is fastened on said reservoir and includes at least one axial tab that co-operates with a shoulder that is secured to said body so as to prevent said reservoir from moving axially in said body;

wherein the actuator element is a one-piece integral construction.

7. An inhalation-synchronized fluid dispenser device comprising:

a body provided with a mouthpiece, a reservoir containing a fluid and a propellant gas, the reservoir configured to be axially slidable in said body during actuation, a metering valve including a valve member being assembled on said reservoir for selectively dispensing the fluid;

an actuator element that is movable and/or deformable between a non-actuation position wherein the reservoir is axially blocked to preclude said metering valve from being actuated, and an actuation position wherein the reservoir is configured to axially slide in the body to permit said metering valve to be actuated; and an inhalation-controlled trigger system including an inhalation-sensitive member that is deformable and/or movable under the effect of inhaling, said inhalation-sensitive member, when deformed and/or moved, moving and/or deforming said actuator element from its non-actuation position towards its actuation position;

said actuator element being a blocking element that, in the non-actuation position, co-operates with the body and with the reservoir so as to prevent said reservoir from moving axially in the body, wherein said actuator element is a blocking ring that is fastened on said reservoir and includes at least one axial tab that co-operates with a shoulder that is secured to said body so as to prevent said reservoir from moving axially in said body;

wherein the blocking ring includes two axial tabs in addition to the at least one axial tab and wherein all three axial tabs of the blocking ring co-operate with the shoulder to prevent the reservoir from moving axially in the body.

* * * * *